(12) United States Patent
Anderson et al.

(10) Patent No.: US 6,306,130 B1
(45) Date of Patent: Oct. 23, 2001

(54) APPARATUS AND METHODS FOR REMOVING BLOOD VESSELS

(75) Inventors: Richard Rox Anderson, Lexington, MA (US); Christine C. Dierickx, Tielt-Winge (BE)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/287,872

(22) Filed: Apr. 7, 1999

Related U.S. Application Data

(60) Provisional application No. 60/081,062, filed on Apr. 7, 1998.

(51) Int. Cl.$^7$ ...................................................... A61M 1/00
(52) U.S. Cl. .................................. 606/27; 606/9; 606/10; 606/13; 607/88; 607/96; 607/100
(58) Field of Search ................................ 606/2, 3, 9, 10, 606/11, 12, 13, 27; 607/88, 89, 90, 91, 93, 94, 96, 98, 100, 101, 108; 128/898

(56) References Cited

U.S. PATENT DOCUMENTS

| | | | |
|---|---|---|---|
| 5,344,418 | 9/1994 | Ghaffari | 606/9 |
| 5,344,434 | * 9/1994 | Talmore | 607/88 |
| 5,522,813 | 6/1996 | Trelles | 606/2 |
| 5,531,739 | 7/1996 | Trelles | 606/2.5 |
| 5,558,667 | 9/1996 | Yarborough et al. | 606/9 |
| 5,707,403 | * 1/1998 | Grove et al. | 607/89 |
| 5,759,200 | 6/1998 | Azar | 607/89 |
| 5,879,376 | 3/1999 | Miller | 607/89 |

FOREIGN PATENT DOCUMENTS

| | | | |
|---|---|---|---|
| WO 96/18433 | 6/1996 | (WO) | A61N/5/06 |

OTHER PUBLICATIONS

Dierickx et al., "Clinical and Histological Responses of Blood Vessels to Long (msec) 532 nm Laser Pulses", *Lasers Surg. Med.*, 8:33, Abstract 266 (1996).
Gabay et al., "Modelling the Assessment of Port Wine . . . Following a Diagnostic Laser Pulse", *Lasers in Surgery and Medicine*, 20:179–187, (1997).
Goldman et al., "Photothermal Sclerosis of Leg Veins", *Dermatol Surg.*, 22:323–330, (1996).
Hsia et al., "Treatment of Leg Telangiectasia Using a Long–Pulse Dye Laser at 595 nm", *Lasers in Surgery and Medicine* 20:1–5 (1997).
Lahaye et al., "Optimal Laser Parameters for Port Wine Stain Therapy:a Theoretical Approach", *Phys. Med. Biol.*, 30:573–587, (1985).
van Gemert et al., "Non–invasive determination of port wine stain . . . optimal laser treatment strategies", *Phys. Med. Biol.*, 42:937–950, (1997).

(List continued on next page.)

*Primary Examiner*—Linda C. M. Dvorak
*Assistant Examiner*—R. Kearney
(74) *Attorney, Agent, or Firm*—Fish & Richardson P.C.

(57) ABSTRACT

Methods and apparatus for inducing necrosis and degradation of blood vessels are described. The invention is suitable to treat various conditions such as varicose veins and telangiectasia. The apparatus for inducing degradation of a blood vessel in a tissue, e.g., skin, includes an external energy source that non-invasively delivers to the blood vessel energy that is preferentially absorbed by the blood vessel to heat the blood vessel walls to a temperature of at least about 60 degrees centigrade, and a pressure source connected to the energy source to collapse the blood vessel once the blood vessel walls have been heated to at least about 60 degrees centigrade for a period of time and with a force sufficient to permanently weld the apposed walls of the blood vessel together, whereby the blood vessel undergoes necrosis and degradation.

31 Claims, 5 Drawing Sheets

OTHER PUBLICATIONS van Gemert et al., "Wavelengths for port win stain laser . . . radius and skin anatomy", *Phys. Med. Biol.* 42:41–50, (1997).

van Gemert et al., "Treatment of Port–Wine Stains: Analysis", *Medical Instrumentation*, 21:213–217, (1987).

van Gemert et al., "Is There An Optimal Laser Treatment for Port Wine Stains?", *Lasers in Surgery and Medicine*, 6:76–83 (1986).

van Gemert et al., "Temperature behaviors of a model port–wine . . . coagulation", *Phys. Med. Biol.*, 27:1089–1104, (1982).

* cited by examiner

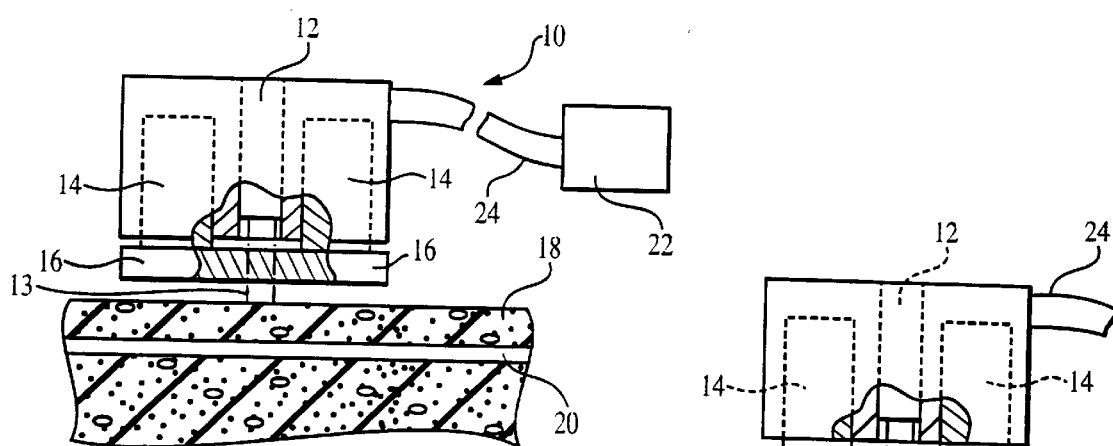
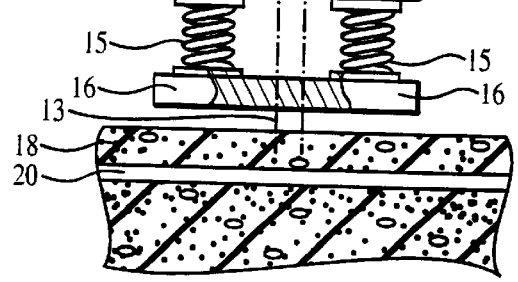
FIG. 1
FIG. 1A
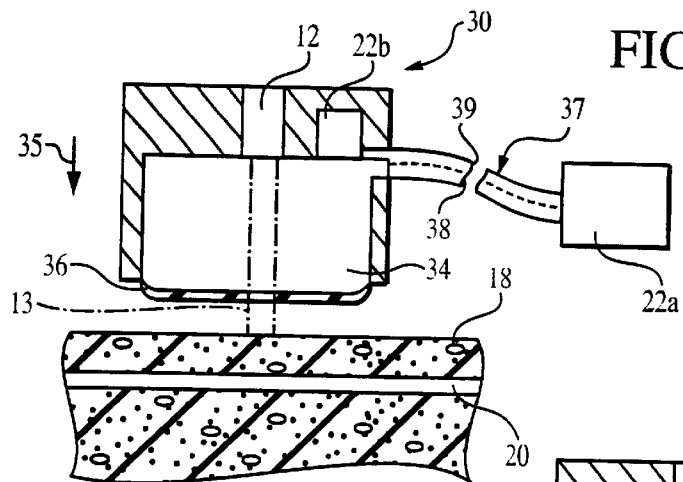
FIG. 2A
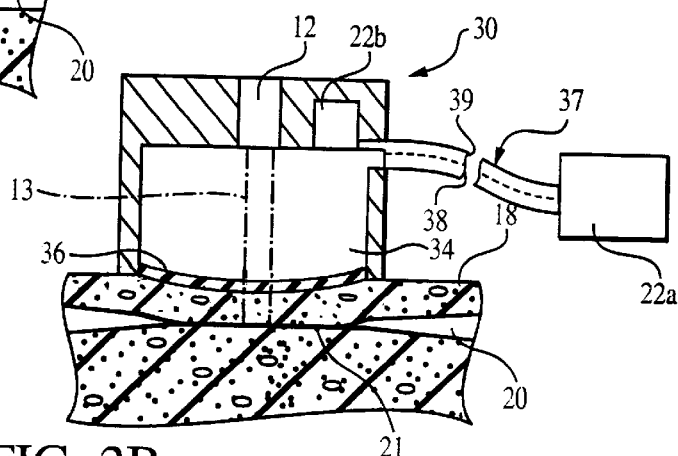
FIG. 2B

APPARATUS AND METHODS FOR REMOVING BLOOD VESSELS

CROSS-REFERENCE TO RELATED APPLICATION

This application claims priority from U.S. Provisional Application Ser. No. 60/081,062, filed Apr. 7, 1998.

This invention was made with Government support under an SBIR grant awarded by the National Institutes of Health. The government may have certain rights in the invention.

FIELD OF THE INVENTION

This invention relates to methods and apparatus for inducing blood vessel necrosis of unwanted or diseased, e.g., dilated, blood vessels.

BACKGROUND OF THE INVENTION

A blood vessel can be any vascular structure, e.g., an artery, a vein, or a capillary. A dilated blood vessel is usually associated with any one or more of a variety of disease conditions, e.g., telangiectasias and varicose veins.

Telangiectasias are skin manifestations of primary cutaneous disorders and systemic diseases. For example, linear telangiectasias are seen on the faces of patients with actinically damaged skin and acne rosacea and are found on the legs of patients with venous hypertension and essential telangiectasia. Mat telangiectasias are lesions of broad macules and are commonly found on the face, oral mucosa, and hands of patients.

Cutaneous disorders associated with telangiectasias include acne rosacea, actinically damaged skin, venous hypertension, essential telangiectasia, ionizing radiation, and Poikiloderma vasculare atrophicans. Telangiectasias are also associated with systemic diseases such as carcinoid, ataxia-telangiectasia, mastocytosis, dermatomyositis, xeroderma pigmentosa, scleroderma, lupus erythematosus, hereditary hemorrhagic telangiectasia, and cirrhosis.

Varicose veins are dilated, tortuous superficial veins that result from defective structure and function of the valves of the veins, from intrinsic weakness of the vein wall, or rarely from arteriovenous fistulas. Varicose veins can be categorized as primary or secondary. Primary varicose veins originate in the superficial system while secondary varicose veins result from deep venous insufficiency and incompetent perforating veins, or from deep venous occlusions causing enlargement of superficial veins that serve as collateral veins.

Patients with varicose veins are often concerned about the cosmetic appearance of their legs, but varicose veins are also often associated with various physical symptoms as well. For example, symptoms can include a dull ache or pressure sensation in the legs after prolonged standing. In addition, extensive venous varicosities may cause skin ulcerations near the ankles. Superficial venous thrombosis may be a recurring problem and rarely a varicosity ruptures and bleeds, leading to more severe symptoms.

Treatments for dilated blood vessels, especially varicose veins, include sclerotherapy and surgical therapy. In sclerotherapy, a sclerosing solution such as hypertonic saline or surfactants is injected into the involved blood vessels, which results in deformation of the vascular structure. Surgical therapy involves extensive ligation and stripping of the greater and lesser saphenous veins. However, administration of these therapies usually requires high technical skill. Furthermore, the common patients, fear of needles and surgical procedures prevents many from seeking these treatments.

Laser and other light sources have also been used in photothermolysis therapy to treat dilated blood vessels, such as varicose veins. Selectively-absorbed light, e.g., in the form of pulses, is used to damage the vessels while sparing the surrounding tissues. However, reperfusion of treated blood vessels reduces the effectiveness of the treatment. Multiple treatments are often required because of reperfusion of a treated vessel. In addition, reperfusion of a treated vessel is undesirable because of clotting factors and thrombolytic factors associated with the process. Photothermolysis therapy is in common use for lack of a better alternative despite the relatively high cost, number of treatments, and risk of post-treatment pigmentation.

SUMMARY OF THE INVENTION

The invention is based on the discovery that by non-invasively heating the walls of a blood vessel to a temperature of at least about 60° C., and then forcibly pressing together or collapsing the walls for a time sufficient to allow them to cool, the vessel walls become adhered or "welded" together, resulting in closure of the vessel lumen, irreversible necrosis and degradation, and thus removal of the blood vessel during the subsequent healing. The new non-invasive methods greatly reduce reperfusion of a treated vessel, and substantially improve the efficacy of conventional photothermolysis therapy.

In general, the invention features a non-invasive method of inducing necrosis and degradation of a blood vessel, e.g., a dilated vein, in a tissue, such as skin, by non-invasively heating walls of the blood vessel to a temperature of at least about 60 (and up to about 100) degrees centigrade, and collapsing the blood vessel by applying pressure (e.g., 1 to 10 atmospheres) to the tissue surrounding the blood vessel for a period of time and with a force sufficient to collapse the blood vessel and to permanently weld the apposed walls of the blood vessel together, whereby the blood vessel undergoes necrosis.

The energy source can be an optical source, such as a pulsed or scanned optical source, e.g., a laser, or it can be a flash lamp, e.g., a xenon flash lamp. Ultrasound and radio frequency energy sources can also be used. For example, the optical source can be a visible or near-infrared optical source that emits in a wavelength range of 500 to 1100 nanometers and delivers optical energy with exposure durations of, e.g., 1 to 100 or 5 to 50 milliseconds.

The pressure has to be applied at the right time, e.g., after heating is completed, for example, when blood within the vessel is vaporized. For example, pressure can be applied within one thermal relaxation time of the blood vessel after the vessel walls are heated to at least 60 degrees centigrade. The pressure must also be maintained for an adequate time, e.g., at least one thermal relaxation time of the blood vessel. Pressure can be applied by mechanical compression, hydraulic compression, or pneumatic compression.

The new method can be used to remove unwanted blood vessels in a variety of disorders including varicose veins, acne rosacea, actinically damaged skin, venous hypertension, telangiectasia, Poikiloderma vasculare atrophicans, vascular malformations, hemangioma, ataxia-telangiectasia, lupus erythematosus, hereditary hemorrhagic telangiectasia, and cirrhosis.

In another aspect, the invention features an apparatus for inducing necrosis and degradation of a blood vessel in a tissue. The apparatus includes an external energy source that delivers energy, e.g., non-invasively, to the blood vessel that is preferentially absorbed by the blood vessel (for a time sufficient) to heat the blood vessel walls to a temperature of at least about 60 degrees centigrade, and a pressure source connected to the energy source to apply pressure, e.g., non-invasively, to the blood vessel once the blood vessel walls have been heated to at least about 60 degrees centigrade for a period of time and with a force sufficient to collapse the blood vessel and to permanently weld the apposed walls of the blood vessel together, whereby the blood vessel undergoes necrosis.

The energy source can be an optical source, e.g., a laser, such as an alexandrite, semiconductor diode, Nd:YAG, dye, copper vapor, argon ion, or krypton ion laser, or a flash lamp. The energy source can also be a radio frequency generator or an ultrasound generator. For example, the optical source can be a visible or near-infrared optical source that emits in a wavelength range of 500 to 1100 nanometers and delivers optical energy with exposure durations, e.g., pulses, of, for example, 1 to 100 or 5 to 50 milliseconds.

In different embodiments, the pressure source can be a hollow chamber filled with pressurized air that compresses skin when the chamber is placed in contact with the skin, or a solid or flexible surface or plate that presses against the tissue, thereby indirectly compressing the blood vessel. The pressure can be 1 to 10 atmospheres.

The apparatus can further include a cooling source, such as a sapphire block, which is in contact with a skin area exposed to the energy source during the heating of the blood vessel. For example, the cooling source can cool the skin area when the pressure source applies pressure to the blood vessel.

The apparatus can further include timing and/or control circuitry to initiate compression by the pressure source within one thermal relaxation time of the blood vessel after the vessel walls are heated to at least 60 degrees centigrade, and/or timing/control circuitry that maintains compression by the pressure source for at least one thermal relaxation time, e.g., 2, 3, or 10 or more relaxation times, of the blood vessel.

"Removal" of a blood vessel results when the vessel degrades during healing after treatment.

When a procedure, e.g., heating or compressing, is performed on a blood vessel "non-invasively," the blood vessel is not exposed surgically, and is not directly contacted by a device used to carry out the procedure, e.g., a device that heats or compresses the blood vessel. For example, for heating, a device can be used that delivers energy to the vessel, through surrounding tissue, without touching the vessel. For compressing, the device can press on tissue surrounding the vessel, which then indirectly compresses the vessel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides numerous advantages. For example, the new methods are simple to apply, are non-invasive, are more effective than prior methods, and provide permanent removal of undesired blood vessels by degradation during healing.

Other features and advantages of the invention will be apparent from the following detailed description, and from the claims.

BRIEF DESCRIPTION OF THE DRAWINGS

FIG. 1 is a schematic diagram of a mechanical vein removal device.

FIG. 1A is a schematic diagram of an alternative mechanical vein removal device.

FIG. 2A is a schematic diagram of a blood vessel removal device that operates using fluid.

FIG. 2B is a schematic diagram of a vessel removal device in use to forcibly compress the tissue surrounding a target blood vessel.

DETAILED DESCRIPTION

Figure 3A:
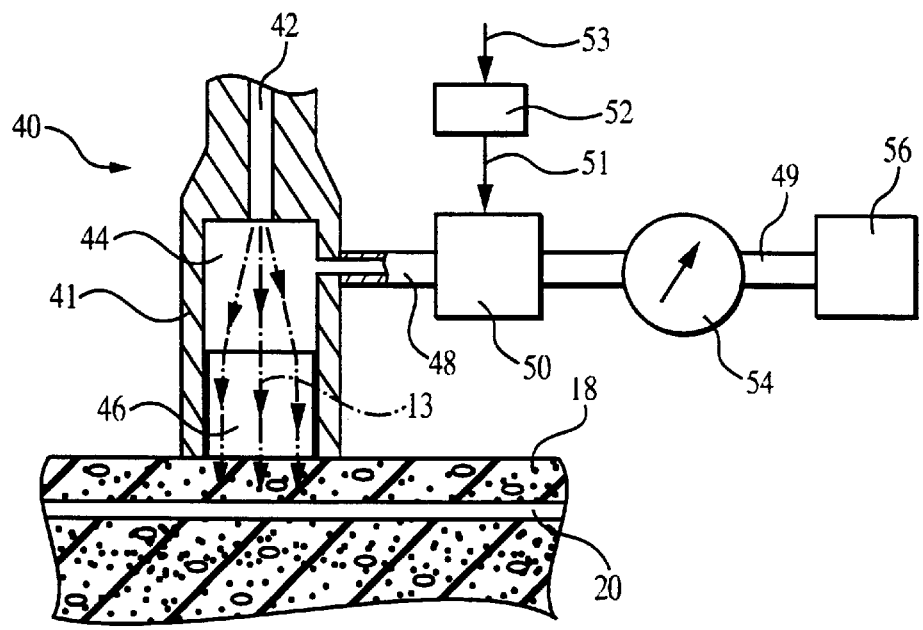
FIG. 3A is a schematic diagram of a vessel removal device that operates using fluid pressure on an optically transparent, piston-like block or window.

Perfusion (blood flow) is necessary to maintain a blood vessel. Indeed, perfusion of blood is the defining quality of blood vessels. Conversely, when a vessel is closed off and perfusion stops, the vessel will eventually thrombose, die, and degrade. The new non-invasive methods make selective use of this natural process.

The invention provides methods and apparatus useful for non-invasively inducing selective necrosis of unwanted blood vessels. According to the present invention, a blood vessel, for example in the skin, is selectively heated non-invasively, by an external energy source, and subsequently squeezed or compressed indirectly by a timed pressure source to close the vessel lumen, and to bring the walls of the blood vessel into direct and close contact for a time sufficient to permanently weld them together, in effect ligating the vessel, which then undergoes necrosis and degrades, thereby removing the unwanted blood vessel.

General Methodology

The new methods induce irreversible blood vessel necrosis by selectively heating a target blood vessel and welding the apposed walls of the blood vessel together. Selective heating of a target blood vessel can be achieved by various methods known in the art. An external energy source that is capable of delivering energy in a wavelength preferentially absorbed by a blood vessel, as opposed to surrounding tissues, is suitable for selectively heating and thermo-damaging the walls of the blood vessel.

Blood vessels contain red blood cells which are rich in hemoglobin. Hemoglobin provides a chromophore that is absent in the surrounding tissues, e.g., dermis. Therefore, hemoglobin (and the oxygenated form, oxyhemoglobin) is a suitable target for selective absorbance of heat energy within blood vessels. Other chromophores, e.g., FDA approved dyes such as methylene blue, that selectively absorb energy can be artificially added to the blood vessel as well, but require injection, which is an invasive procedure, and would be considered a separate step prior to carrying out the new, non-invasive methods.

Various energy sources can be employed to deliver or emit a beam of energy that selectively heats blood vessels. These sources include, but are not limited to, light sources (e.g., at wavelengths associated with sufficient absorption by blood hemoglobins), radio frequency generators, and a ultrasound generators. A light source can be any existing optical source, e.g., a laser or a flash lamp, that emits light at a wavelength absorbed by a naturally occurring chromophore in the blood such as hemoglobin. Preferably a light source is a pulsed or scanned optical source capable of emitting radiation at a wavelength in a range of about 500 to about 1100 nanometers. Many commercially available laser systems are suitable for practicing the present invention, e.g., a 532 nm (green) KTP laser (Laserscope, Palo Alto, Calif.), 585–600 nm pulsed dye lasers (Candela, Wayland, Mass.), 800 nm diode lasers (Laserlite, Boston, Mass.), 900–1000 nm diode lasers (Palomar, Lexington, Mass.), 755 nm alexandrite lasers (Cynosure, Wayland, Mass.), and 1064 nm Nd YAG laser (Nidek, Fremont, Calif.). Flash lamps, such as xenon flash lamps, can also be used as the optical energy source.

As an alternative to optical energy sources, ultrasound (G.E. Medical Systems, Waukistah, Wash., Siemens Medical, Issaquah, Wash.) and radio frequency (RF)(Valley Lab, Yellow Springs, Ohio) energy sources can be used. However, ultrasound and RF energy is not selectively absorbed by blood vessels, and thus must be aimed or focused at the vessels to achieve selective heating. Such focusing methods and devices are known in this field.

Selectively heating the blood in a blood vessel raises the temperature of the blood within the vessel and as a result raises the temperature of the endothelial cells of the vessel wall, causing them to be damaged. According to the present invention, a target blood vessel should be heated to a temperature of at least about 60° centigrade up to about 75° centigrade as a minimum temperature. The denaturation temperature of type I and type III collagens in the blood vessel walls vary between about 60 to about 75° centigrade. Higher temperatures of about 100° centigrade provide additional advantages, as described below. Without being limited to any technical explanation, it appears that a temperature of about 60° to 75° centigrade is useful for adequately welding collagen-containing materials such as blood vessel walls together.

The total time that a given temperature is maintained to achieve denaturation and the temperature to which the vessel walls need to be heated can be correlated; the higher the temperature (between 60° C. and 75° C.), the less time that the temperature needs to be maintained. For each degree centigrade, the time required changes by about a factor of two. Thus, to decrease the maintained heating time by 10 seconds, one must increase the temperature at which the blood vessel wall must maintained by about 3° C.

In a preferred embodiment, a target blood vessel is quickly and selectively heated to a temperature at which blood within the vessel is vaporized (boiled), i.e., above 100° C. It is important to avoid "cooking" the skin too much by heat conduction. Rapid and selective heating minimizes skin damage, but the skin can also be cooled externally to help prevent thermal damage. Typically, heating for one location on a blood vessel is completed within the time of one laser pulse (e.g., a continuous wave laser turned on and off in rapid succession, or a pulsed laser), but multiple laser pulses directed at the same location on the blood vessel can also be used.

Generally, when the blood temperature is quickly heated to about 100° C., vapor cavities (or bubbles) occur within the vessel. The rapid expansion of a vapor cavity within the vessel pushes blood away in both directions and clears most of the blood from the heated region of the vessel lumen. Subsequent collapsing of the vapor cavity brings the opposed vessel walls into contact, but typically does not provide the apposition required to allow the walls to become permanently welded together.

When cavitation occurs and the optical pulse (exposure duration) of a laser, e.g., a 532 nm KTP laser, is 1 msec or greater, the expanding vapor cavity clears away blood from the region of vessel exposed to the laser light pulse. However, pulse widths of 10 to 20 msec, or longer, are preferred. The vapor cavity collapses on the millisecond time scale, though larger cavities have a longer lifetime. To make best use of this cavitation process, compression of the heated blood vessel should be precisely timed to coincide with the beginning of, or duration of, the collapse of the cavity.

It is advantageous to remove the blood from the blood vessel after heating and before applying pressure to the vessel. This can be accomplished by gentle vaporization as described above, or can also be achieved by any other suitable means. For example, the blood can be squeezed out of a region within a blood vessel by simply applying pressure to the corresponding skin area of the blood vessel region after a temperature of at least about 60° C. is achieved. However, blood should not be removed prior to heating, e.g., not before the end of the laser pulse, because the blood is what absorbs the energy.

Generally, the exposure duration, e.g., laser pulse width, should be less than or approximately equal to the thermal relaxation time or cooling time of a target blood vessel to avoid unnecessary thermal damage to the overlying skin. The thermal relaxation time of a blood vessel is the time that it takes for the vessel to cool down to half of a given peak temperature. For a given vessel, the thermal relaxation time in seconds is approximately equal to the square of the vessel's diameter in millimeters. For example, a 1.0 mm diameter leg vein takes about 1.0 second to cool to one half of a given peak temperature. For a 0.5 mm diameter vein, the thermal relaxation time is about 0.25 seconds, and for a 0.25 mm diameter vein, the thermal relaxation time is about 0.0625 seconds, or 62.5 milliseconds.

In the case of an optical energy source which emits radiation at a wavelength from about 500 to 1100 nanometers, the radiation is generally applied for a time of about 1 to 100milliseconds, e.g., about 5 to 500, 10 to 300, or 20 to 100 milliseconds. For the blood vessels found to be unwanted, this is best accomplished by a laser or other optical energy pulse of 5 to 100 milliseconds. Pulse lengths (widths) for RF and ultrasound energy sources are also in the same range.

In general, pressure must be applied externally to bring the vessel walls into direct and close contact and to hold them together for a time sufficient to effect a permanent sealing or "welding" together of the walls. The selective heating creates a collagen gel at the damaged vessel walls, and this gel connects the tissues of the apposed vessel walls to form the "weld." Typically, to obtain a weld of sufficient strength, pressure must be applied after the vessel walls have been heated to a temperature of about 60° C., and before the vessel walls have had a chance to cool to below about 60° C., i.e., within the thermal relaxation time. In general, pressure is applied within a fraction of a second, e.g., 10, 100, 500, 1000 or more milliseconds, after a target blood vessel is exposed to heating energy. The pressure can be initiated after or during the pulse. For the 1.0 mm diameter blood vessel example described above, pressure is typically applied within less than 1.0 second after heating is completed.

The length of time that pressure is applied is also on the order of at least one thermal relaxation time. Thus, pressure is applied for at least 1.0 second in the 1.0 mm diameter blood vessel example. For a smaller vessel, the minimum time for applying pressure is less. However, for all vessel sizes, it is preferred to apply pressure for longer times, e.g., 2 to 10 times the thermal relaxation time, to ensure adequate cooling while pressure is being applied.

Blood Vessel Removal Devices

The new methods can be performed by new devices that apply the energy required to heat the blood vessel walls, and that apply the required pressure at the correct time and for the required duration. These devices thus include both energy and pressure delivery means, as well as the requisite control and timing mechanisms.

Pressure can be applied to a target blood vessel using any device or mechanism that can apply the necessary pressure for the required period of time. For example, mechanical compression, hydraulic compression, or pneumatic compression can be applied to the skin area above a target blood vessel to collapse the target blood vessel and weld the walls together to permanently close the vessel lumen. The amount of pressure applied must be sufficient to bring the heated vessel walls fully into contact. At a minimum, this is somewhat greater than the blood pressure, which is at most about 1/3 atmosphere (atm). However, stronger welds occur with higher apposition pressure, and an applied pressure of 1 to 10 atm should be used.

Mechanical compression can be delivered by touching and pressing an object against the skin surface at the same site where the heating energy is delivered and within one thermal relaxation time after the heating energy is delivered. This can be achieved, for example, by delivering the heating energy through the same component used for compression of the skin area, if that component is transparent to the heating energy. There are several readily available hand held laser systems with windows or lenses which can be held in direct mechanical contact with the treated skin area. However, these require a high degree of skill to operate, because they lack any mechanism to provide a precisely timed, reliable application of pressure. As described in further detail below, a new device includes one or more solenoids attached to a hand held laser system that forcefully drives a transparent contact window, lens, or platform into the skin at a precise time, e.g., within the thermal relaxation time after the heating energy is delivered.

For example, FIG. 1 shows a mechanical, solenoid-actuated blood vessel removal device 10 including a laser output device 12 that emits a laser beam 13 onto tissue 18, e.g., skin, to strike blood vessel 20. The vein removal device 10 is connected to a control mechanism 22 via cable 24. The control mechanism 22 can include a laser source, in which case cable 24 includes an optical cable connected to laser output device 12. In the alternative, laser output device 12 can include a small battery operated laser source.

Laser output device 12 emits a laser pulse of sufficient duration and power to heat blood vessel (e.g., vein) 20 to at least 60° C. The laser beam 13 passes through plate or window (lens) 16, which is made of a material transparent to the particular laser light wavelength used, e.g., sapphire or silica. The plate can also be opaque, except for a laser transparent window or lens in an appropriate location on the plate.

Once the laser pulse or pulses have heated the vessel 20 to the appropriate temperature, solenoids 14 are actuated to move pressure plate or window 16 downwards to contact and press on the surface of tissue 18, which, in turn, presses on the vessel 20. In general, the solenoids are activated within one thermal relaxation time period after the laser pulse, which is calculated as described herein for the particular target vessel 20. The control mechanism 22 includes a timing mechanism triggered by the laser output and a signaling mechanism (not shown) that controls solenoids 14. Alternatively, the timing and control mechanisms can be included within the mechanical vein removal device 10. These timing and control mechanisms are commercially available, and known to those of skill in this field. For example, a delay generator manufactured by Stanford Research can be used.

Once actuated, pressure plate 16 is held forcibly against the tissue 18 to compress vessel 20 for a time sufficient to allow welding to occur. Alternatively, the pressure can be applied to plate 16 by a spring 15 arranged between solenoids 14 and the plate (FIG. 1A). This is typically at least one thermal relaxation time period, and can be several times the thermal relaxation time. The pressure generated by plate 16 on the skin is on the order of 1 to 10 atmospheres. If a spring is used, the amount of pressure applied to the skin is controlled by the size and nature of the spring.

Hydraulic compression can also be carried out by several methods. For example, a transparent fluid in a chamber can be brought into direct contact with the treated skin area. The pressure of the fluid in the chamber can be adjusted to increase or decrease compression.

Hydraulic compression can be applied alone or in combination with mechanical compression. For example, in a hybrid hydraulic-mechanical system, a flexible membrane in contact with the treated skin area can be forcibly compressed into the skin area by injecting fluid into a chamber behind the membrane. Such a combination has the advantage of providing more uniformly timed compression because of the flexibility of the membrane, as well as allowing excellent control over the timing and force of the compression.

Pneumatic compression can also be employed, for example using the pressure created by jets of air impinging directly onto the skin above a treated vessel, or pressure created by a hybrid pneumatic-mechanical system. Hybrid mechanical-pneumatic and mechanical-hydraulic systems can be similar in construction. For example, a mechanical-pneumatic system can include a transparent balloon or flexible membrane driven by a pneumatic chamber to deliver pressure to a target blood vessel in a timely and controlled manner.

FIG. 2A shows an alternative blood vessel removal device 30 that operates using fluid, i.e., hydraulic or pneumatic, pressure. As in FIG. 1, device 30 includes a laser output device 12, but in place of pressure plate or window 16 includes a flexible membrane 36, e.g., of an elastic material such as natural or synthetic rubber, silicone rubber, TEFLON@, polyethylene, or polycarbonate plastics. The membrane can be reusable or disposable. Flexible membrane 36 seals the open end of fluid chamber 34, which is coupled to an external pressure source through fluid conduit 38. Device 30 is connected to a control mechanism and fluid pressure source 22a by a dual cable 37 that includes electrical and/or optical conduits 39 and fluid conduit 38. The fluid can be air, for a pneumatic device, or any liquid, such as water or oil, e.g., mineral, hydrocarbon, or vegetable oil, for a hydraulic device.

In use, device 30 is moved into contact with tissue 18 (arrow 35). After laser output device 12 emits a laser pulse of sufficient duration to heat blood vessel 20 to at least about 60° C., fluid chamber 34 is filled with pressurized air or liquid, causing flexible membrane 36 to expand and forcibly compress tissue 18 as shown in FIG. 2B. The pressure of flexible membrane 36 causes the opposed walls of blood vessel 20 to contact each other for a time sufficient to be permanently welded together in the region 21 of blood vessel 20 corresponding to the region of tissue 18 contacted by flexible membrane 36.

The fluid pressure source 22a can be an air compressor or a hydraulic pump that forces liquid into fluid chamber 34. Device 30 can optionally include control circuitry 22b to control the timing of filling of fluid chamber 34 to occur within one thermal relaxation time after the laser heating for a given blood vessel. In the alternative, all control circuitry and mechanisms can be within control and fluid pressure source 22a.

FIG. 3A shows another embodiment of a pneumatically (or hydraulically) driven blood vessel removal device 40, including a housing 41, an optic fiber 42 (connected to an optical, e.g., laser, source, not shown here), a hollow chamber 44, and sliding block or window 46, made of a laser transparent material, such as sapphire, silica, glass, acrylic, or other plastics. Device 40 is connected to a valve 50, e.g., a solenoid valve, via fluid conduit 48, and valve 50 is connected to a pump or pressure source 56, via pressure regulator 54 and conduit 49. Valve 50 is controlled by timing circuitry 52 via electrical (or mechanical) conduit 51, and timing circuitry 52 is controlled by a laser trigger output 53 from the laser source (not shown here).

Device 40 is linked to an optical source (laser) by a fiber optic cable or fiber. Light (e.g., laser) beam 13 passes through block or window 46, and selectively heats blood vessel 20. Valve 50 is actuated within the thermal relaxation time after an optical pulse heats the vessel to deliver regulated pressure (pneumatic or hydraulic) to the piston-like block or window 46, which slides downwards within chamber 44 to compress tissue 18 to achieve timed compression of blood vessel 20.

Figure 3B:
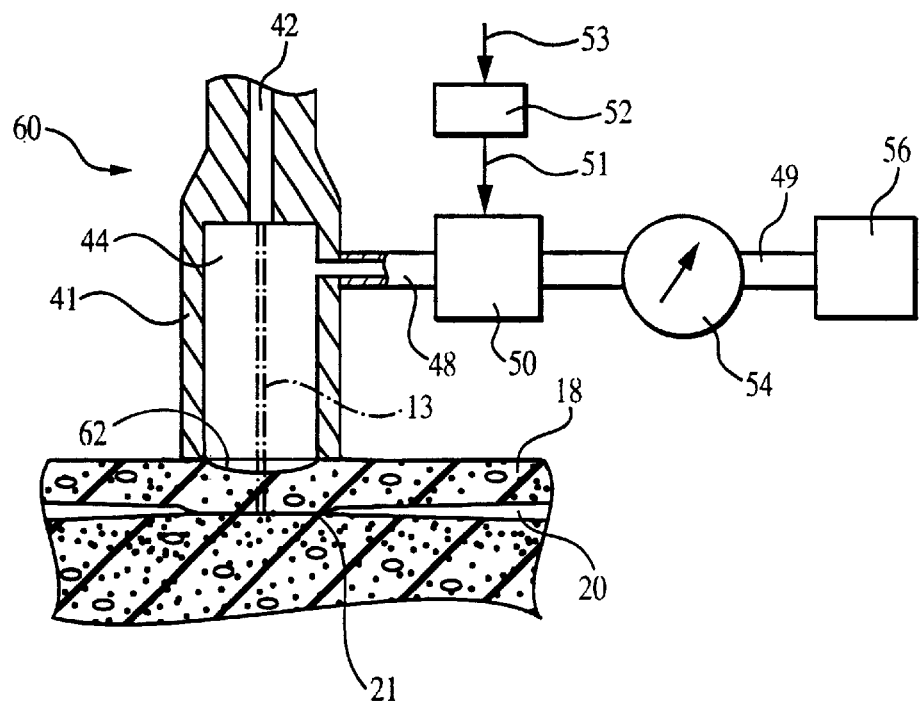
FIG. 3B is a schematic diagram of a vessel removal device that forcibly compresses the tissue surrounding a target blood vessel using air pressure directly contacting the tissue.

FIG. 3B shows another blood vessel removal device 60, which is quite similar to device 40 in FIG. 3A, except that it does not include a window or block 46. Instead, hollow chamber 44 is open at its distal end. Device 60 is preferably pneumatic, and uses air pressure to compress tissue, e.g., skin, 18. Device 60 is pushed against the skin above a target blood vessel 20 with sufficient pressure to seal chamber 44 against the skin. The optic source is activated to generate a light beam directed through optic fiber 42 onto the skin 18. A lens (not shown) can be used to increase the spot size of beam 13.

Once optic beam 13 heats vessel 20 to a sufficient temperature, e.g., after a predetermined period of time, valve 50 is actuated to allow pressurized air to enter chamber 44, under control of pressure regulator 54 and timing circuitry 52 as above, and thus press onto skin 18. The compressed air within chamber 14 creates a compressed downward bulge 62 in skin 18, which causes blood vessel 20 to become collapsed in region 21. Once actuated, air pressure is maintained to forcibly compress tissue 18 to compress vessel 20 for a time sufficient to allow welding to occur. This is typically at least one thermal relaxation time period, and preferably several times the thermal relaxation time. The pressure generated within chamber 44 on the skin can be on the order of 1 to 10 atmospheres.

Device 60 can also be outfitted with a flexible membrane covering the opening of chamber 44, similar to membrane 36 in FIG. 2A.

The new procedures are often effective with a single treatment but, if required, can be administered more than once to a patient in need of such treatment. In general, one or several passes of the device over the target vessel should be sufficient to cause permanent welding and subsequent necrosis. If additional treatment is required, it can be performed at intervals of several weeks to a month. The procedure can also be modified to reduce post-treatment complications and to make a patient physically and psychologically more comfortable during the treatment.

For example, the treated skin area can be cooled before, during, or after treatment. The treated skin area can be cooled by holding a cooled sapphire handpiece (or cooled pressure plates) in direct contact with the skin before, during, and/or after a pulse of energy is delivered. In addition, a longer pulse width, e.g., significantly longer than the thermal relaxation time of the epidermis, can be used to allow energy to be delivered at a lesser intensity, and to allow heat to be extracted from the skin surface during each pulse of energy such that the epidermis stays cool. The skin or other target tissue can also be cooled using cold compressed air that is applied simultaneously with pressure.

In addition, a cooling mechanism can be coupled to the pressure source. For example, when mechanical, hydraulic, or pneumatic compression is applied, the pressing object, fluid, or air within the compression system can be cooled to produce a cooling effect on the skin surface. For example, cold air or liquids can be used to fill the fluid chamber 16 and thereby cool the flexible membrane 36 that applies pressure to the target tissue 18.

The invention will be further described in the following examples, which do not limit the scope of the invention described in the claims.

EXAMPLES

Animal and human studies can be used to investigate the therapeutic effects of the methods and apparatus described herein.

Example 1

Rabbit Study of Microvascular Response to Photothermal Treatment Alone

Ear blood vessels in three size ranges (50–150 $\mu$m, 200–400 $\mu$m, and 1 mm) of 24 albino rabbits were exposed to a single KTP laser pulse of various pulse widths and fluences. In each animal, laser exposures were performed for a period of 1 to 30 or 1 to 60 msec (laser exposure duration), and at 8 fluence increments. Each vessel was observed individually at various time points after the exposure, i.e., immediately, 5 minutes, 10 minutes, 2 hours, and 3 hours after the exposure. Gross vessel responses (vasodilation, vasoconstriction, thrombosis, hemorrhage, vessel disappearance) were assessed via an operating microscope.

The treated sites were then biopsied, fixed in formalin, processed for paraffin-embedded histology, and stained with hematoxylin and eosin. Histology was performed to determine the selectivity and extent of microvascular thermal injury.

Selectivity of microvascular injury was determined by the extent of perivascular collagen denaturation as assessed by loss of type I collagen birefringence in the surrounding dermis. Type I collagen has a specific helix-coil transition near 70° C. which destroys birefringence. Histologically, the vessel contents, endothelium, surrounding dermis, and overlying epidermis were scored for thermal and other injury.

For a given vessel size and laser pulse duration, increasing fluence caused a vessel to undergo vasodilation, transient intravascular coagulum (embolized after the pulse), vasoconstriction (due to collagen denaturation), and vessel disappearance. The vessel disappearance was due to essentially complete emptying of blood from the vessel, which was confirmed histologically and by transillumination of the ear. Vasoconstriction was always correlated with histological evidence of transmural vessel wall injury. Threshold fluence for vasoconstriction was studied systematically as a function of laser pulse duration for all three vessel sizes. The threshold fluence for vasoconstriction and vessel wall injury increased with vessel diameter (FIGS. 4–6).

Figure 4:
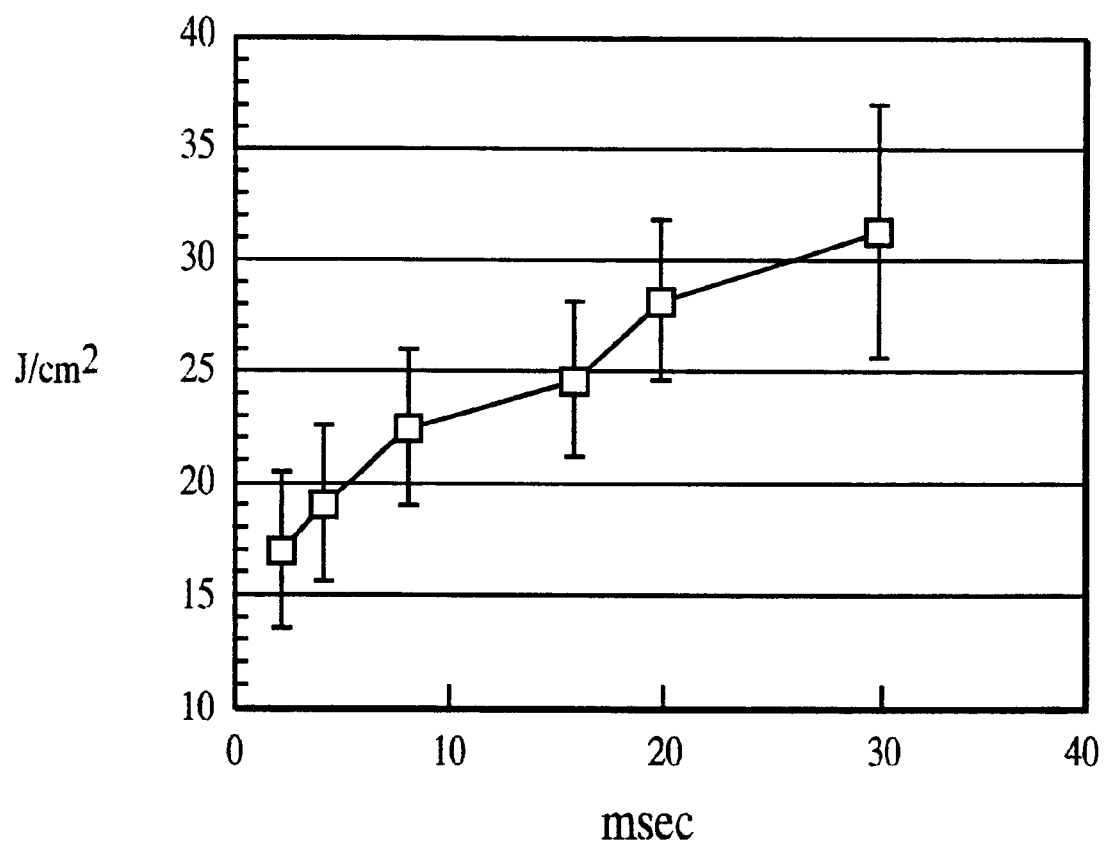
FIG. 4 is a graph of threshold fluence for vasoconstriction vs. pulse width using a 532 nm KTP laser (160 $\mu$m vessel group, n=60) on a rabbit ear vessel. Points shown are mean, bars are standard deviation.

FIG. 4 shows a graph of threshold fluence for vasoconstriction (J/cm$^2$) vs. pulse width (msec) for blood vessels of about 160 $\mu$m in diameter (n=60). Points shown on the graph are mean, bars are standard deviation. As pulse width increased, the threshold fluence required for vasoconstriction also increased.

Figure 5:
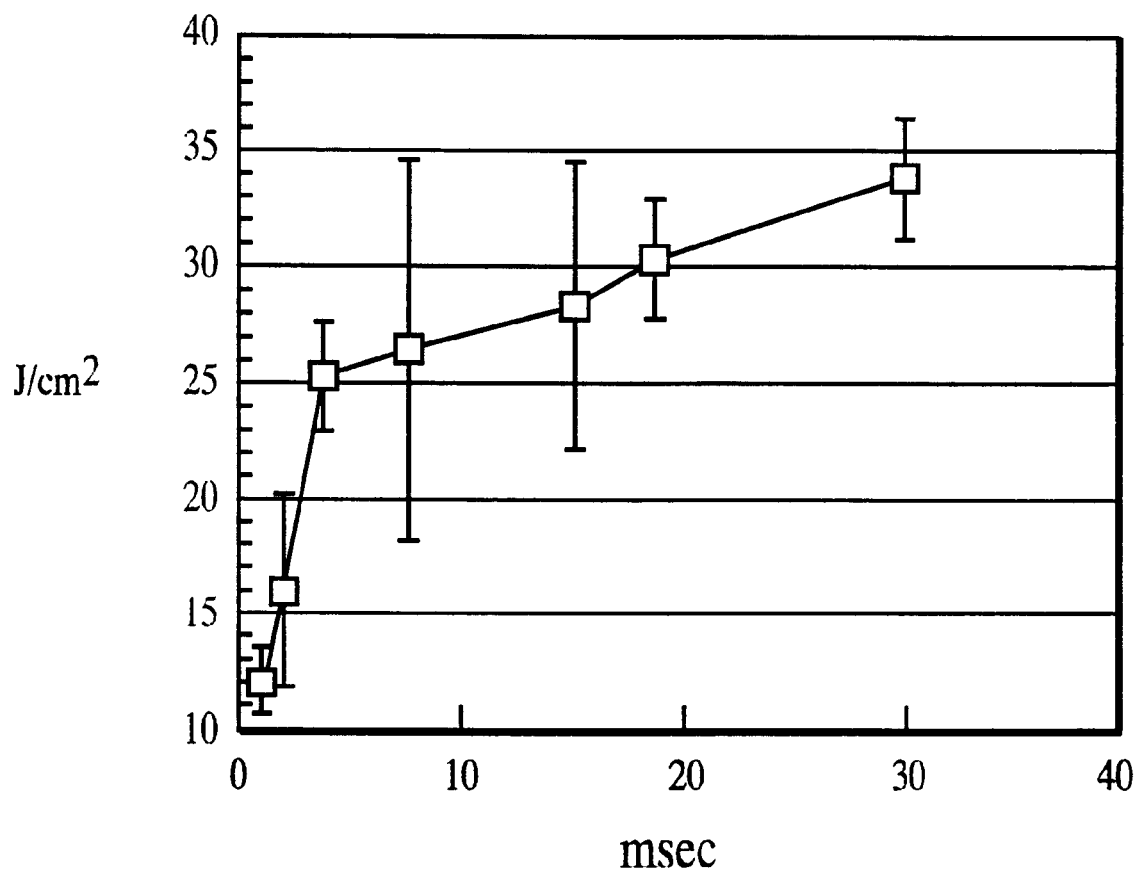
FIG. 5 is a graph of threshold fluence for vasoconstriction vs. pulse width using a 532 nm KTP laser (320 $\mu$m vessel group) on a rabbit ear vessel. Points shown are mean, bars are standard deviation.

FIG. 5 shows a graph of threshold fluence for vasoconstriction (J/cm$^2$) vs. pulse width (msec) for larger blood vessels, about 320 $\mu$m in diameter. Points shown are mean, bars are standard deviation. As in FIG. 4, as pulse width increased, the threshold fluence required for vasoconstriction also increased, but much more rapidly at pulse widths less than 5 milliseconds.

Figure 6:
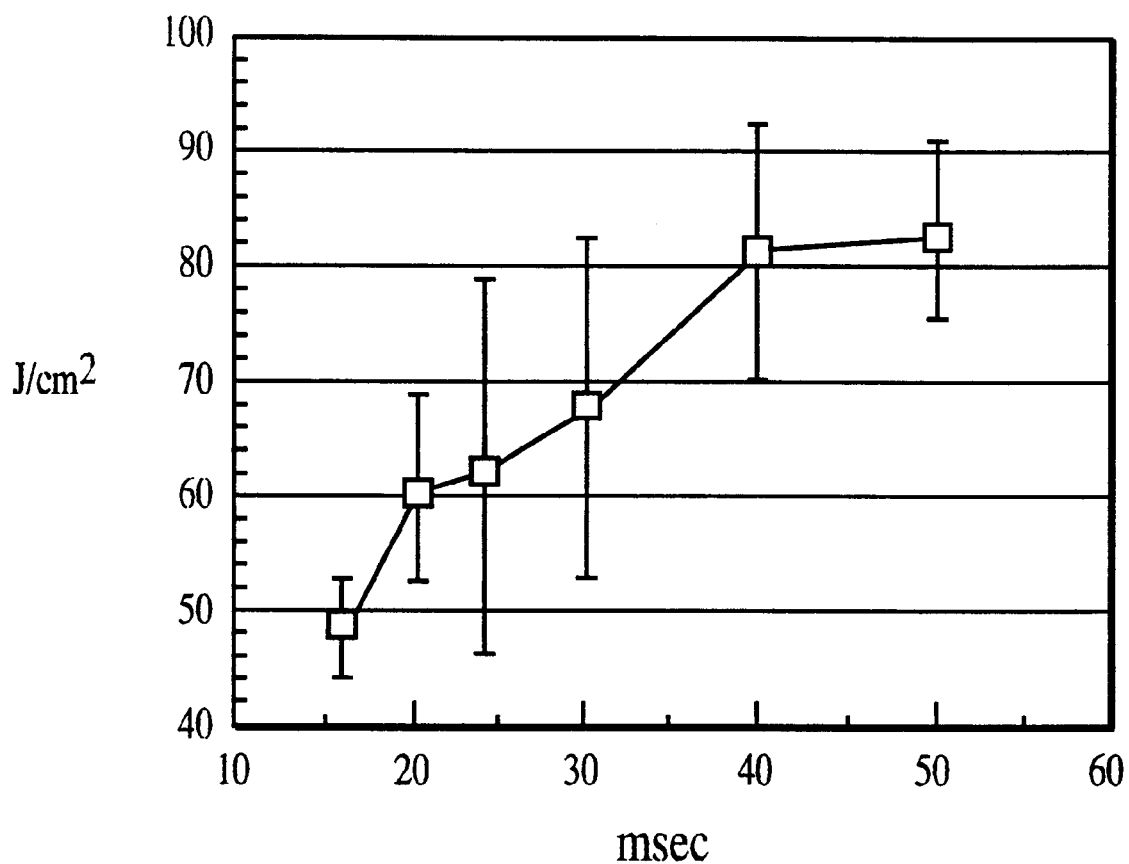
FIG. 6 is a graph of threshold fluence for vasoconstriction vs. pulse width using a 532 nm KTP laser (1 mm vessel group) on a rabbit ear vessel. Points shown are mean, bars are standard deviation.

FIG. 6 shows another graph of threshold fluence for vasoconstriction (J/cm$^2$) vs. pulse width (msec), this time for vessels about 1.0 mm in diameter. Points shown are mean, bars are standard deviation. Again, as pulse width increased, the threshold fluence required for vasoconstriction also increased.

Histology at and above threshold fluences for vasoconstriction showed endothelial cell damage and swelling, with loss of perivascular collagen birefringence extending typically 10–20 $\mu$m around the vessel adventitia. At the vasoconstriction thresholds, there was no damage to dermis away from vessels. Interestingly, damage was also minimal even at 2 to 3 times this threshold, suggesting a saturation effect of some nature. Epidermal injury, when present, was focal and located near large vessels consisting of basal cell elongation. In no case were the vessels ruptured. Hemorrhage was never observed.

The absence of either blood or a coagulum was consistently found in vessels exposed to the threshold fluence for vasoconstriction, or greater. These "empty selectively cooked" vessels were strikingly different from the vessels treated with a 585 nm, 0.4 msec pulsed dye laser which displayed local hemorrhages and a residual intravascular coagulum. These vessels were also different from the vessels treated with a conventional c.w. laser in which more extensive dermal injury was produced due to heat conduction.

Thermal injury in all vessels greater than 100 $\mu$m was asymmetric, with broader perivascular collagen denaturation on the side toward the laser source. However, at the vasoconstriction threshold and above, perivascular collagen denaturation extended all the way around vessels, even for the vessels of 1.0 mm diameter.

Based on the microscopical observations and the histological findings, threshold fluences were established for vasoconstriction and perivascular collagen damage for each pulse width for blood vessels of three different diameters. The results are summarized in Table 1.

TABLE 1

Threshold Fluences (THF) for Vasoconstriction (VC) and Perivascular Collagen Damage (PVCD)

| 160 $\mu$m | | | 320 $\mu$m | | | 1 mm | | |
|---|---|---|---|---|---|---|---|---|
| Pulse Width (msec) | THF for VC (J/cm$^2$) | THF for PVCD (J/cm$^1$) | Pulse Width (msec) | THF for VC (J/cm$^2$) | THF for PVCD (msec) | Pulse Width (msec) | THF for VC (J/cm$^2$) | THF for PVCD (J/cm$^2$) |
| 1 | — | — | 1 | 12.2 | — | 15 | 48.7 | 45.5 |
| 2 | 16.9 | — | 2 | 16 | — | 20 | 59.8 | 54.6 |
| 4 | 19 | — | 4 | 25.5 | 28 | 25 | 60.3 | 64.3 |
| 8 | 22.4 | 25.3 | 8 | 26.2 | 31.5 | 30 | 68 | 68 |
| 15 | 24.6 | 26.4 | 15 | 28 | 34.5 | 40 | 81 | 84.5 |
| 20 | 28.2 | 27.3 | 20 | 30 | 36.5 | 50 | 83.4 | 88.5 |
| 30 | 31.3 | 31.2 | 30 | 33.5 | 40.8 | — | — | — |

Suitable pulse width-fluence combinations were identified based on gross vasoconstriction and the histological picture of endothelial damage characterized by a fine rim of perivascular collagen denaturation. Suitable pulse widths for the 160 $\mu$m and 320 $\mu$m diameter vessel groups were from 4–30 msec, while for the 1 mm diameter vessel group were from 16–50 msec.

This study clearly shows that KTP laser exposures in the 1 to 30 or 50 msec range cause selective thermal injury of cutaneous microvessels. The fluence necessary for vessel injury increases with vessel diameter. The pulse durations "ideal" for welding of the vessel wall also appears to increase with vessel diameter. The data provide a useful "matrix" of KTP laser exposure parameters appropriate for photothermolysis of different vessel sizes. Thus, this study provides the optimum KTP laser pulse width for use with the new blood vessel removal methods. These results are useful for future human clinical trials and are predictive of the effectiveness of the laser treatment in humans. Similar studies can be conducted with different lasers or other energy sources such as flash lamps and ultrasound to obtain data for optimum pulse times and energy levels.

Example 2
Rabbit Study of Microvascular Response to Photothermal and Compression Treatment Ear blood vessels in three size ranges (50–150 μm, 200–400 μm, and 1 mm) of 24 albino rabbits are exposed to a single KTP laser pulse of various pulse widths and fluences and then forcibly compressed by application of external pressure. In each animal, laser exposures are performed for a period of 1–30 msec (laser exposure duration), and at 8 fluence increments. The KTP laser hand piece is fitted with a mechanical compression lens mounted on a spring, the other end of which is moved by a solenoid at precise time intervals corresponding to the laser pulses. The timing of the solenoid actuation is controlled by a commercially available delay generator (Stanford Research).

Alternatively, the laser handpiece is fitted with a fluid chamber covered by a flexible membrane that can be inflated with cool air or a liquid such as water or mineral oil from an external pressure source through a fluid conduit. The flexible membrane is controlled to be inflated and pressed forcibly against the skin by a standard timing and control mechanism.

Compression is applied at 2.5 to 20 milliseconds after completion of the laser pulse for the 50–150 μm diameter vessels, and is maintained for a period of 1000 milliseconds. Compression is applied at 40 to 100 milliseconds after the laser pulse for the 200–400 μm diameter vessels, and is maintained for a period of 1000 milliseconds. Compression is applied at 100 milliseconds after the laser pulse for the 1.0 mm diameter vessels, and is maintained for a period of 3000 milliseconds.

Each vessel is observed individually at various time points after the exposure and compression, i.e., immediately, 5 minutes, 10 minutes, 2 hours, and 3 hours after the exposure. Gross vessel responses (vasodilation, vasoconstriction, thrombosis, hemorrhage, vessel disappearance) are assessed via an operating microscope.

The treated sites are then biopsied, fixed in formalin, processed for paraffin-embedded histology, and stained with hematoxylin and eosin. Histology is performed to determine the selectivity and extent of microvascular thermal injury as well as sealing or welding of the apposed vessel walls.

As noted in Example 1, for a given vessel size and laser pulse duration, increasing fluence causes a vessel to undergo vasodilation, transient intravascular coagulum (embolized after the pulse), vasoconstriction, and the desired "vessel disappearance." The initial vessel disappearance is due to essentially complete emptying of blood from the vessel (caused by rapid heating of the blood within the target vessel to about 100° C. and resulting gentle vaporization), which can be confirmed histologically and by transillumination of the ear. The compressive force that welds the walls of the blood vessels together (when the walls are heated to a temperature of over 60° C.) accounts for the irreversible and permanent disappearance of the blood vessels.

Suitable pulse width-fluence combinations are identified based on gross vasoconstriction and the histological picture of endothelial damage characterized by a fine rim of perivascular collagen denaturation. Suitable pulse widths for the 160 μm and 320 μm diameter vessel groups are from 4–30 msec, while for the 1.0 mm diameter vessel group are from 16–50 msec.

This study shows that KTP laser exposures in the 1–30 msec range combined with application of an external compressive force cause selective welding of cutaneous microvessels. The fluence necessary for vessel welding increases with vessel diameter. The pulse durations useful for welding of the vessel wall also increase with vessel diameter. Results are useful for human clinical trials and are predictive of the effectiveness of the laser treatment in humans.

Example 3
Treatment of Human Leg Telangiectasia

A semiconductor diode laser of 800 nm (near-infrared) wavelength, emitting in a pulse width of 5 to 30 msec (Star Medical Technologies, Inc.) is used to treat human leg telangiectasia. Pulses are delivered through an optical hand piece which provides refractive index matching, a square output aperture of 9 by 9 mm, and cooling of the skin surface to 10° C. The hand piece is fitted with a fluid chamber covered by a flexible membrane that can be inflated with cool air or a liquid such as water or mineral oil from an external pressure source through a fluid conduit. The flexible membrane is controlled to be inflated and pressed forcibly against the skin by a standard timing and control mechanism. Alternatively, the laser is fitted with a mechanical compression plate driven by a solenoid at precise time intervals corresponding to the laser pulses.

The leg telangiectases are classified according to vessel diameter and clinical appearance such as blue, red, linear, arborizing, or spider. The vessel diameter is measured from computer images taken with a polarized CCD camera. The size of the vessels can range from about 0.1 mm to 3.0 mm.

Twenty-five patients are treated at 8 test sites in the legs with a range of fluences (20–50 J/cm$^2$) and pulse widths (5 to 20 milliseconds). Of the 8 treatment sites, 4 receive 1 treatment once a month; while the remaining 4 receive up to three treatments per month. The possible additive effect of multiple pulses is evaluated by treating the sites with triple pulses given at a repetition rate of 0.5 Hz. Blinded analysis of results is obtained by presenting polarized photographs of treatment fields to a panel of observers not involved in the study.

For a vein with a diameter of 1.0 mm, the vein removal device delivers a compression force to the skin immediately above the target vein within 100 milliseconds of completion of the laser pulse, and maintains the pressure for 3000 milliseconds. For a vein with a diameter of 3.0 mm, the device delivers a compression force to the skin immediately above the target vein within 100 milliseconds, and maintains pressure for 20 seconds.

The immediate response after laser treatment is either vessel thrombosis or vessel disappearance. Vessel "disappearance" means that the blood was emptied from the vessel lumen. It is believed that gentle (slow) intravascular cavitation at a pressure less than the bursting pressure of venule (caused by rapid heating of the blood within the target vessel to about 100° C.) accounts for the phenomenon of the immediate vessel disappearance, and that the compressive force that welds the walls of the blood vessels together (when the walls are heated to a temperature of about 60° C.) accounts for the irreversible and permanent disappearance of the blood vessels.

Selectivity of the laser treatment can be provided by the use of multiple pulses as well as by the use of a specific range of wavelength and pulse width. For example, when large vessels are treated, application of energy in a longer pulse, e.g., greater than 50 msec, enables the skin to be cooled during the pulse without simultaneous cooling the large vessel.

Other Embodiments

Other embodiments are within the following claims.

We claim:

1. A method of inducing a blood vessel in a tissue to degrade, the method comprising:

non-invasively heating walls of the blood vessel to a temperature of at least about 60 degrees centigrade, and subsequently collapsing the blood vessel and applying sufficient pressure to maintain the blood vessel in a collapsed state for at least one thermal relaxation time of the blood vessel to permanently weld the apposed walls of the blood vessel together, whereby the blood vessel undergoes necrosis and degrades.

2. The method of claim 1, wherein the blood vessel is collapsed by applying pressure to the tissue surrounding the blood vessel for a period of time and with a force sufficient to permanently weld the apposed walls of the blood vessel together.

3. The method of claim 2, wherein the tissue is skin, and the pressure is applied externally to the skin.

4. The method of claim 1, wherein blood within the blood vessel is heated to a temperature of at least about 100 degrees centigrade.

5. The method of claim 1, wherein blood within the blood vessel is heated to a temperature at which it vaporizes.

6. The method of claim 1, wherein heating is accomplished by an optical source, a radio frequency generator, or an ultrasound generator.

7. The method of claim 6, wherein the optical source is a pulsed or scanned optical source.

8. The method of claim 1, wherein heating is accomplished by a laser.

9. The method of claim 1, wherein heating is accomplished by an optical source that emits optical energy in a wavelength range of 500 to 1100 nanometers.

10. The method of claim 1, wherein heating is accomplished by an optical source that delivers optical energy with exposure durations of 1 to 100 milliseconds.

11. The method of claim 1, wherein the blood vessel is collapsed after blood within the vessel is vaporized.

12. The method of claim 1, wherein the blood vessel is collapsed within one thermal relaxation time of the blood vessel after the vessel walls are heated to at least 60 degrees centigrade.

13. A method of claim 1, wherein a pressure of 1 to 10 atmospheres is applied to collapse the blood vessel.

14. The method of claim 1, wherein pressure is applied by mechanical compression, hydraulic compression, or pneumatic compression.

15. The method of claim 1, wherein the blood vessel is a vein.

16. The method of claim 1, wherein the blood vessel is a varicose vein.

17. The method of claim 1, wherein the blood vessel is associated with a cutaneous disorder selected from the group consisting of acne rosacea, actinically damaged skin, venous hypertension, telangiectasia, Poikiloderma vasculare atrophicans, vascular malformations, and hemangioma.

18. The method of claim 1, wherein the blood vessel is associated with a systemic disease selected from the group consisting of ataxia-telangiectasia, lupus erythematosus, hereditary hemorrhagic telangiectasia, and cirrhosis.

19. A non-invasive apparatus for inducing a blood vessel in a tissue to degrade, the apparatus comprising an energy source adapted to non-invasively deliver energy to the blood vessel to heat the blood vessel walls to a temperature of at least about 60 degrees centigrade, a pressure source connected to the energy source, and a control mechanism that directs the pressure source to apply pressure to the blood vessel after the blood vessel walls have been heated to at least about 60 degrees centigrade with a force sufficient to collapse the blood vessel and for a time period of at least one thermal relaxation time of the blood vessel to permanently weld the apposed walls of the blood vessel together, whereby the blood vessel undergoes necrosis and degrades.

20. The apparatus of claim 2, wherein the energy source is an optical source, a radio frequency generator, or an ultrasound generator.

21. The apparatus of claim 19, wherein the energy source is a laser.

22. The apparatus of claim 21, wherein the laser is an alexandrite, semiconductor diode, Nd:YAG, dye, copper vapor, argon ion, or krypton ion laser.

23. The apparatus of claim 19, wherein the energy source is an optical source that emits optical energy in a wavelength range of 500 to 1100 nanometers.

24. The apparatus of claim 19, wherein the energy source is an optical source that delivers optical energy with exposure durations of 1 to 100 milliseconds.

25. The apparatus of claim 24, wherein the optical source delivers optical energy with exposure durations of 5 to 50 milliseconds.

26. The apparatus of claim 19, wherein the pressure source applies pressure via mechanical compression, hydraulic compression, or pneumatic compression.

27. The apparatus of claim 19, wherein the pressure source comprises a solid or flexible surface that presses against the tissue, thereby applying non-invasive pressure and indirectly compressing the blood vessel.

28. The apparatus of claim 19, wherein the pressure source applies a pressure of 1 to 10 atmospheres.

29. The apparatus of claim 19, further comprising a cooling source that is in contact with the tissue exposed to the energy source during the heating of the blood vessel.

30. The apparatus of claim 29, wherein the cooling source cools the tissue when the pressure source applies pressure to the blood vessel.

31. The apparatus of claim 19, further comprising control circuitry to initiate compression by the pressure source within one thermal relaxation time of the blood vessel after the vessel walls are heated.

* * * * *

UNITED STATES PATENT AND TRADEMARK OFFICE
CERTIFICATE OF CORRECTION

PATENT NO. : 6,306,130 B1
DATED : October 23, 2001
INVENTOR(S) : Richard Rox Anderson and Christine C Dierickx It is certified that error appears in the above-identified patent and that said Letters Patent is hereby corrected as shown below:

Column 1,
Line 65, delete "patients," and insert -- patients' --

Column 6,
Line 57, delete "100milliseconds" and insert -- 1000 milliseconds --

Column 16,
Line 24, delete "claim 2" and insert -- claim 19 --

Signed and Sealed this

Thirty-first Day of August, 2004

JON W. DUDAS
*Director of the United States Patent and Trademark Office*